United States Patent [19]

Deger et al.

[11] Patent Number: 4,578,469

[45] Date of Patent: Mar. 25, 1986

[54] BENZO[DE]PYRANO[3,2-G]ISOQUINOLINE DERIVATIVES USEFUL AS DYESTUFFS

[75] Inventors: Hans-Matthias Deger, Hofheim am Taunus; Rüdiger Erckel, Eppstein; Horst Frühbeis, Kelkheim, all of Fed. Rep. of Germany

[73] Assignee: Hoechst Aktiengesellschaft, Frankfurt, Fed. Rep. of Germany

[21] Appl. No.: 655,307

[22] Filed: Sep. 26, 1984

Related U.S. Application Data

[63] Continuation of Ser. No. 380,350, May 20, 1982, abandoned.

[30] Foreign Application Priority Data

May 22, 1981 [DE] Fed. Rep. of Germany ....... 3120402

[51] Int. Cl.⁴ .................................... C07D 471/04
[52] U.S. Cl. .................................... 546/66; 544/310; 544/317; 544/319; 544/320; 544/324; 544/327; 544/328; 544/331
[58] Field of Search ............... 544/322, 310, 317, 319, 544/320, 324, 327, 328, 331; 546/66

[56] References Cited

U.S. PATENT DOCUMENTS

| | | |
|---|---|---|
| 3,014,041 | 12/1961 | Hausermann et al. |
| 3,749,727 | 7/1973 | Fuchs et al. ............... 546/47 |
| 3,910,912 | 10/1975 | Scheurmann et al. ............... 544/284 |
| 3,920,704 | 11/1975 | Augart et al. ............... 544/79 |
| 3,947,450 | 3/1976 | Fuchs et al. ............... 546/47 |
| 4,002,630 | 1/1977 | Papenfuhs . |
| 4,077,961 | 3/1978 | Gunther et al. |

FOREIGN PATENT DOCUMENTS 2006253  5/1979  United Kingdom .

Primary Examiner—Donald G. Daus
Assistant Examiner—William A. Teoli, Jr.
Attorney, Agent, or Firm—Curtis, Morris & Safford

[57] ABSTRACT

Coumarin compounds of the general formula (1)

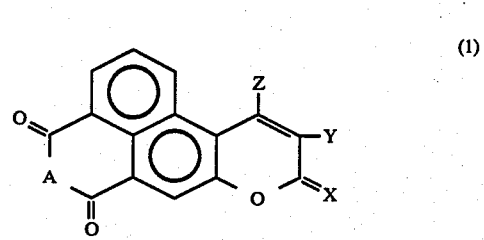

in which A denotes an oxygen atom or a grouping >N—R in which R represents a hydrogen atom or an alkyl radical of 1 to 18 carbon atoms which may be substituted by fluorine, chlorine or bromine atoms or by alkoxy$_{C_1-C_4}$, dialkyl$_{C_1-C_4}$-amino, —SO$_2$—N(alkyl$_{C_1-C_4}$)$_2$ or cyano groups or a cycloaliphatic, aromatic or heterocyclic radical which may be substituted by fluorine, chlorine or bromine atoms or by alkyl$_{C_1-C_4}$, alkoxy$_{C_1-C_4}$, hydroxyl, cyano, sulfonamide or —SO$_2$—N—(alkyl$_{C_1-C_4}$)$_2$ groups, X denotes an oxygen atom or a grouping ≧N—R' in which R' represents a hydrogen atom or an alkyl$_{C_1-C_{18}}$carbonyl, alkoxy$_{C_1-C_4}$carbonyl, alkyl$_{C_1-C_4}$carbamoyl or alkyl$_{C_1-C_4}$sulfonyl group or an aryl, arylcarbonyl, arylcarbamoyl or arylsulfonyl radical which may be substituted by fluorine, chlorine or bromine atoms or by alkyl or alkoxy groups of 1 to 4 carbon atoms each or by cyano groups, Y denotes a hydrogen atom or a cyano or an alkyl$_{C_1-C_4}$ carboxylate group, an aryl, arylsulfonyl or —CO—O—aryl radical which may be substituted by fluorine, chlorine or bromine atoms or by alkyl or alkoxy groups of 1 to 4 carbon atoms, or by nitro, methylenedioxy, amino, monoalkyl$_{C_1-C_4}$amino or dialkyl$_{C_1-C_4}$amino groups or by a benzoxazolyl radical, or a heterocyclic radical which may be quaternized and which may be substituted by fluorine, chlorine or bromine atoms or by alkyl or alkoxy groups of 1 to 4 carbon atoms, or by nitro, phenyl, alkyl$_{C_1-C_4}$phenyl, alkoxy$_{C_1-C_4}$phenyl, cyano, methylenedioxy or alkyl$_{C_1-C_4}$ carboxylate groups, and Z denotes a hydrogen atom or an alkyl$_{C_1-C_4}$ carboxylate or cyano group, a process for their preparation, and their use for dyeing or printing synthetic fiber materials, in particular polyester fibers.

8 Claims, No Drawings

BENZO[DE]PYRANO[3,2-G]ISOQUINOLINE DERIVATIVES USEFUL AS DYESTUFFS

This application is a continuation of application Ser. No. 380,350, filed May 20, 1982, now abandoned.

The invention relates to new coumarin compounds of the general formula (1)

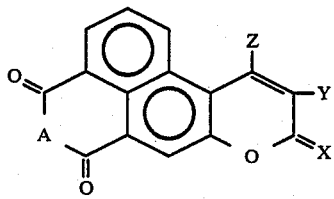
(1)

in which A denotes an oxygen atom or a grouping >N—R in which R represents a hydrogen atom or an alkyl radical of 1 to 18 carbon atoms which may be substituted by fluorine, chlorine or bromine atoms or by, for example, alkyl$_{C_1-C_4}$, dialkyl$_{C_1-C_4}$amino, —SO$_2$—N(alkyl$_{C_1-C_4}$)$_2$ or cyano groups or a cycloaliphatic, aromatic or heterocyclic radical which may be substituted by, for example, fluorine, chlorine or bromine atoms or by alkyl$_{C_1-C_4}$, alkoxy$_{C_1-C_4}$, hydroxyl, cyano, sulfonamide or —SO$_2$—N(alkyl$_{C_1-C_4}$)$_2$ groups, possible examples of a cycloaliphatic radical being a cyclopentyl, cyclohexyl or cycloheptyl radical, of an aromatic radical a phenyl or naphthyl radical and of a heterocyclic radical a pyridine, pyrimidine, benzoxazol-2-yl, benzothiazol-2-yl or benzimidazol-2-yl radical, X denotes an oxygen atom or a grouping N—R' in which R' represents a hydrogen atom or an alkyl$_{C_1-C_{18}}$carbonyl, alkoxy$_{C_1-C_4}$carbonyl, alkyl$_{C_1-C_4}$carbamoyl or alkyl$_{C_1-C_4}$-sulfonyl group or an aryl group (such as, for example, a phenyl group), arylcarbonyl group (such as, for example, a phenylcarbonyl group), arylcarbamoyl group (such as, for example, a phenylcarbamoyl group) or an arylsulfonyl group (such as, for example, a phenylsulfonyl group), all of which may be substituted by, for example, fluorine, chlorine or bromine atoms or by alkyl or alkoxy groups of 1 to 4 carbon atoms each or by cyano groups, Y denotes a hydrogen atom or a cyano or alkyl$_{C_1C_4}$carboxylate group, an aryl radical (such as, for example, a phenyl radical), arylsulfonyl radical (such as, for example, example, a phenylsulfonyl radical) or —CO—O—aryl radical (such as, for example, a —CO—O-phenyl radical), all of which may be substituted by, for example, fluorine, chlorine or bromine atoms or by alkyl or alkoxy groups of 1 to 4 carbon atoms or by nitro, methylenedioxy, amino, monoalkyl$_{C_1-C_4}$amino, dialkyl$_{C_1-C_4}$amino groups or by a benzoxazolyl radical, or a heterocyclic radical, for example a thiophene, benzothiophene, furan, benzofuran, triazole, imidazole, benzimidazole, thiazole, benzothiazole, oxazole, benzoxazole, thiadiazole, oxadiazole or pyridine radical, which may be quaternized and which may be substituted by, for example, fluorine, chlorine or bromine atoms or by alkyl or alkoxy groups of 1 to 4 carbon atoms or by nitro, phenyl, alkyl$_{C_1-C_4}$phenyl, alkoxy$_{C_1-C_4}$phenyl, cyano, methylenedioxy or alkyl$_{C_1-C_4}$carboxylate groups, and Z denotes a hydrogen atom or an alkyl$_{C_1-C_4}$carboxylate or cyano group, and to a process for their preparation and to their use as dyestuffs for dyeing or printing synthetic fiber materials which may be present in mixture with natural fiber materials.

The dyestuffs of the abovementioned general formula (1) can be prepared by condensing a compound of the general formula (2)

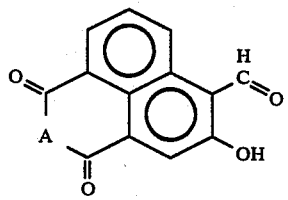
(2)

in which A has the abovementioned meanings with
(a) a compound of the general formula (3)

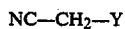
NC—CH$_2$—Y       (3)

in which Y has the abovementioned meanings, in a manner which is in itself known (German Offenlegunsschrift No. 1,619,567) and, as desired, acylating by methods which are in themselves known (German Offenlegungsschrift No. 2,234,207), treating with arylamines or hydrolyzing the resulting iminocoumarin compound of the general formula (4)

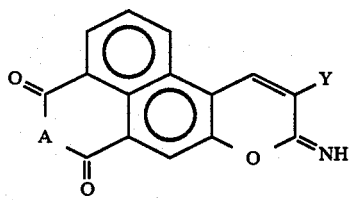
(4)

in which A and Y have the abovementioned meanings, or with
(b) a compound of the general formula (5)

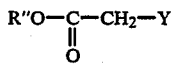
R″O—C—CH$_2$—Y       (5)
       ‖
       O in which Y has the abovementioned meaning and R″ denotes an optionally substituted alkyl or aryl radical, in a manner which is in itself known and, if desired, reacting the resulting coumarin compound of the general formula (6)

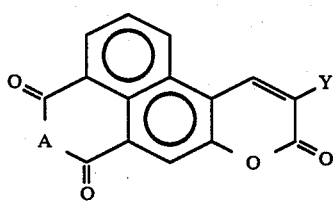
(6)

in which A and Y have the abovementioned meanings, with a cyanide salt by methods which are in themselves known and simultaneously or subsequently treating the addition product which is formed as an intermediate with an oxidizing agent and obtaining a compound of the general formula (7)

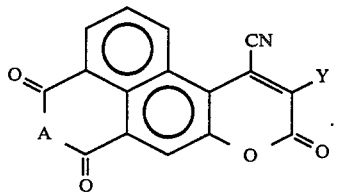
(7)

The compounds (aldehydes) of the abovementioned general formula (2) can be prepared in the way described in German Offenlegungsschrift No. 2,436,032 by heating 3-hydroxynaphthalic anhydride or 3-hydroxynaphthalimide in the presence of a lower aliphatic carboxylic acid, for example formic acid or acetic acid, with hexamethylene-tetraamine or with a mixture of ammonia and formaldehyde in the presence of a small amount of mineral acid, such as sulfuric acid or hydrochloric acid, at temperatures between, preferably, 80° and 100° C.

The condensation of the aldehydes of the general formula (2) mentioned with the compounds of the general formula (3) mentioned is carried out in a polar organic solvent in the presence of inorganic or organic condensing agents and at temperatures between 0° and 100° C., preferably 20° to 80° C. Examples of suitable polar organic solvents are alcohols, in particular lower alkanols, such as methanol or ethanol, further cyclic ethers, such as dioxan or tetrahydrofuran, nitrogen-containing aromatic solvents, such as, for example, pyridine or picoline, and above all amides of lower fatty acids, such as formamide or dimethylformamide. Examples of suitable basic condensing agents are alkali metal salts of carbonic acid, such as sodium carbonate or potassium carbonate, alkali metal salts of lower fatty acids, such as sodium acetate or potassium acetate, and alkali metal alcoholates, such as sodium methanolate, potassium methanolate, sodium ethanolate or potassium ethanolate, and nitrogen bases, such as piperidine or pyrrolidine.

The iminocoumarins of the general formula (4) mentioned are acylated with carboxylic acid halides, chloroformates, carboxylic anhydrides or sulfonic acid halides in a solvent in the presence of an inorganic or organic base, preferably of an amine, at temperatures between 0° and 160° C., preferably 20° and 100° C. Suitable solvents are particularly those of organic nature, such as, for example, hydrocarbons, such as benzene, toluene or xylene, also halogenated hydrocarbons, such as chloroform or chlorobenzene, ethers, such as, for example, diethyl ether, glycol dimethyl ether, dioxan or tetrahydrofuran, or acetone.

Examples of suitable bases for this reaction are alkali metal carbonates, such as sodium carbonate or potassium carbonate, alkali metal salts of lower fatty acids, such as sodium acetate or potassium acetate, and in particular organic bases, such as, for example, triethylamine, pyridine, pyrrolidine or N,N-dimethylaniline. In this reaction, the organic bases can also be used as the solvent.

Examples which may be mentioned of suitable carboxylic anhydrides are acetic anhydride and propionic anhydride and of acid halides are acetyl chloride, chloroacetyl chloride, stearyl chloride, benzoyl chloride, 3-nitrobenzoyl chloride, 3,5-dinitrobenzoyl chloride, 4-chlorobenzoyl chloride, cinnamoyl chloride, methanesulfonyl chloride, ethanesulfonyl chloride, benzenesulfonyl chloride, toluenesulfonyl chloride, 3-methoxypropanesulfonyl chloride, cyanomethanesulfonyl chloride, chloroethanesulfonyl chloride, methyl chloroformate, phenyl chloroformate, β-methoxyethyl chloroformate and diethyl chloroformamide.

The reaction (acylation) of the iminocoumarins of the abovementioned general formula (4) with isocyanates, if appropriate in an inert, anhydrous solvent, such as, for example, toluene, chloroform, chlorobenzene or dioxan, is carried out at temperatures between 0° and 150° C., preferably at 50° to 100°.

The reaction of the iminocoumarins of the general formula (4) mentioned with arylamines, for example anilines, which can be substituted in the aromatic nucleus by fluorine, chlorine or bromine atoms or by alkyl or alkoxy groups of 1 to 4 carbo atoms each or by cyano groups, is effected by methods as described, for example in German Offenlegungsschrift No. 2,226,211. In this reaction, the iminocoumarins are heated, for example together with an aniline derivative, to temperatures of 50°–200° C., preferably to 80°–150° C., and the aniline derivative itself can serve as the solvent. Examples of other solvents suitable for this reaction are alcohols, such as propanol or butanol, glycols and their mono- and di-ethers, preferably glycol monoethyl ether, dimethylformamide, N-methylpyrrolidone and dimethyl sulfoxide. Hydrocarbons, such as toluene and xylene, and chlorinated hydrocarbons, such as chlorobenzene, dichlorobenzene or perchloroethylene, can also be used.

The compounds of the formula (1) mentioned in which X denotes oxygen and Z denotes hydrogen can be prepared by reacting compounds (aldehydes) of the abovementioned general formula (2) with compounds of the general formula (5)

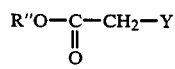
(5)

in which R″ and Y have the abovementioned meanings, under the conditions of the Knoevenagel condensation or by hydrolyzing the iminocoumarins of the abovementioned general formula (4) by methods which are in themselves known. The hydrolysis of iminocoumarin compounds of the general formula (4) to give coumarins of the general formula (1) in which X denotes oxygen and Z denotes hydrogen is carried out in dilute aqueous acids at temperatures between 80° and 120° C. Suitable acids for this purpose are mineral acids, such as hydrochloric acid, hydrobromic acid or sulfuric acid, or even organic acids, such as formic acid, acetic acid or toluenesulfonic acid, in concentrations of 20–200 g/l, preferably of 40–120 g/l.

The condensation of the abovementioned compounds (aldehydes) of the formula (2) with compounds of the general formula (5) is carried out in an organic solvent in the presence of inorganic or organic condensing agents and at temperatures between 50° and 200° C., preferably 80° to 150° C., while simultaneously removing the reaction water. Suitable solvents are hydrocarbons, such as toluene, xylene or cyclohexane, chlorinated hydrocarbons, such as chlorobenzene, chloroform or trichloroethylene, alcohols, such as methanol, ethanol or propanol, or nitrogen-containing solvents, such as pyridine, picoline, dimethylformamide or N,N-dimethylaniline. Suitable condensing agents are alkali metal hydroxides, such as sodium hydroxide or potassium hydroxide, alkali metal alcoholates, such as sodium methanolate, potassium methanolate, sodium ethanolate or potassium ethanolate, nitrogen bases, such as piperidine, pyrrolidone or N-methylaniline, or salts of nitrogen bases, such as piperazine acetate or ammonium acetate.

The compounds of the abovementioned general formula (7) can be prepared by reacting compounds of the general formula (6) mentioned by methods which are in themselves known and described, for example, in German Offenlegungsschrift No. 2,844,299, in a solvent with a cyanide salt, and simultaneously or subsequently treating the addition compounds which are formed here as intermediates with oxidising agents.

The cyanide salts used in this reaction preferably are water-soluble alkali metal cyanides, either as solids or in particular in the form of concentrated aqueous solutions.

Suitable solvents are polar organic solvents such as alcohols, for example methanol, ethanol, isopropanol or ethylene glycol, but in particular aprotic dipolar solvents, such as dimethylformamide, pyridine or picoline.

Suitable oxidizing agents are hydrogen peroxide, persulfates, organic peroxides, such as, for example, dibenzoyl peroxide, nitric acid, bromine or lead tetraacetate.

The reaction involving the cyanide salts is carried out within a temperature range of 0°–100° C., preferably 15°–70° C., and the oxidation is carried out within the range from −10° to 30° C., preferably at −5° to 10° C.

The new coumarin compounds of the formula (1) mentioned are yellow to black-red crystalline powders which give intense green-yellow to red fluorescent solutions in organic solvents, such as alcohols, esters, amides, ethers, ketones or chlorinated hydrocarbons.

The new compounds are suitable for use as dyestuffs on their own or in mixtures with one another or with other dyestuffs, preferably in formulated form, such as, for example, in aqueous dispersion or in solution in organic solvents or in emulsions or dispersions which, in addition to a solvent or a solvent mixture, can also contain water, for dyeing or printing synthetic fiber materials, such as, for example, those comprised of cellulose diacetate, cellulose 2½ acetate, cellulose triacetate or polyamides, such as poly-ε-caprolactam or polyhexamethylenediamine adipate, or also those comprised of polyurethanes or polycarbonates, but in particular those comprised of linear polyesters, such as polyethylene terephthalates.

The abovementioned synthetic fiber materials to be dyed or printed can also be present in mixtures with one another or with natural fiber materials, such as cellulose fibers or wool. For dyeing, they can also be present in various processing states, for example as top, loose stock, yarns or woven or knitted fabrics.

The dyestuffs according to the invention are applied in a manner which is known in principle, as a rule from an aqueous dispersion, but they can also be applied from organic solvents. The dyestuffs can be dispersed, for example by grinding them in the presence of a dispersing agent, such as, for example, in the presence of a product formed by condensing formaldehyde and technical m-cresol and sodium bisulfite and which had been rendered neutral by means of sulfuric acid. For the rest, the dyeing conditions substantially depend on the nature of the synthetic fiber materials present and on their processing state.

For example, shaped cellulose acetate structures are dyed within a temperature range of 75° to 85° C. Cellulose triacetate fibers are dyed at temperatures between about 90° and 125° C. The dyestuffs are applied to polyamide fiber materials within a temperature range between about 90° and 120° C. To dye polyester fiber materials, methods known for this purposes are used and they involve dyeing the fiber material in the presence of carriers, such as o- or p-phenylphenol, methylnaphthalene or methyl salicylate at temperatures of 100° C. to about 130° C. or without the use of carriers at correspondingly higher temperatures, for example between 120° and 140° C. It is also possible to apply the dyestuffs by padding with or without thickeners, for example tragacanth thickener, and to fix them through the action of heat, for example by steam or dry heat for about a ½ to 30 minutes at temperatures within the range from about 100° to 230° C. To improve the fastness to rubbing, the material thus dyed is then advantageously freed from dyestuff adhering to its surface, for example by rinsing or a reductive aftertreatment. This aftertreatment is generally carried out at 60° to 120° C. in an aqueous liquor containing sodium hydroxide solution, sodium dithionite and a nonionic detergent, such as, for example, an ethylene oxide/phenol addition product.

The synthetic fiber materials can be dyed from organic solvents, for example by allowing the dyestuff to exhaust from the solution onto the fiber at room temperature or above, preferably at 70° to 130° C., if appropriate under pressure, or by using a continuous procedure and impregnating woven or knitted fabrics with a dyestuff solution, drying them and subjecting them to a brief heat treatment, for example at temperatures of 180° to 210° C. Examples which may be mentioned of solvents for the exhaustion process are solvents which are not miscible with water and which have boiling points between 40° and 170° C., such as, for example, aliphatic halogenated hydrocarbons, such as methylene chloride, trichloroethane, trichloroethylene or trifluorotrichloroethane. Solvents which are miscible with water, such as, for example, alcohols or dimethylformamide, are also possible, in particular for a continuous dyeing process. The solvents can of course also be in the form of mixtures and contain other auxiliaries which are soluble in the solvents, such as, for example, oxyalkylation products of fatty alcohols, alkylphenols and fatty acids.

To produce prints on the synthetic fiber materials, for example on those made of polyesters, polyamides or cellulose triacetate, the dyestuffs can be used in the form of water-containing formulations which, in addition to the finely divided dyestuff, can also contain suitable thickeners. Fixing is carried out, for example after printing and drying, by steaming at atmospheric pressure or under an elevated pressure of up to 2.5 gage atmospheres for 10 to 60 minutes. Fixing can also be effected by the action of hot air of 160° to 220° C. for 30 seconds to 10 minutes.

The dyestuffs according to the invention are additionally suitable for melt-dyeing, preferably polyethylene terephthalate.

The new dyestuffs according to the invention make it possible to obtain on the fibers, fabrics and plastic compositions mentioned greenish yellow to red fluorescent dyeings which in some cases are extremely brilliant. Compared with hitherto known 5,6-benzocoumarins, the dyeings are distinguished by a high color intensity, good build-up and exhaustion behavior and by very good fastness properties, such as washing, rubbing, sublimation, perspiration and light fastness properties.

The parts indicated in the examples which follow denote parts by weight.

EXAMPLE 1

255 parts of 3-hydroxy-4-formyl-N-methylnaphthalimide and 157 parts of benzimidazolyl-2-acetonitrile were suspended in 5000 parts of dimethylformamide, and 20 parts of piperidine were added with stirring. After stirring for four hours at room temperature, the precipitated product was filtered off with suction, washed with cold ethanol and dried at 50° C. in vacuo. This produced 362 parts (92% of theory) of an orange-colored dyestuff powder of the formula

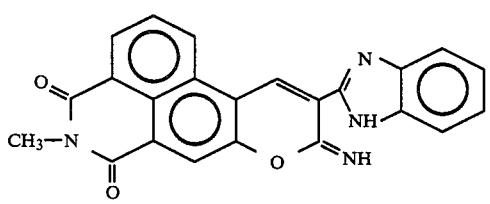

which gave brilliant yellowish red dyeings on polyester fiber materials.

EXAMPLE 2

313 parts of 3-hydroxy-4-formyl-N-(3-methoxy-n-propyl)-naphthalimide and 157 parts of benzimidazolyl-2-acetonitrile were suspended in 3000 parts of dimethylformamide, and 10 parts of piperidine were added with stirring. After stirring for two hours at room temperature, the precipitated product was filtered off with suction, washed with cold ethanol and dried at 50° C. in vacuo. This produced 393 parts (87% of theory) of a yellow dyestuff powder of the formula

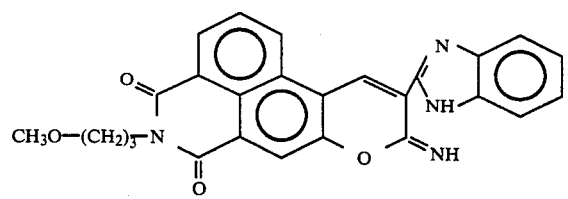

which gave brilliant yellowish red dyeings on polyester fiber materials.

EXAMPLE 3

323 parts of 3-hydroxy-4-formyl-N-cyclohexylnaphthalimide and 157 parts of benzimidazolyl-2-aceonitrile were suspended in 3500 parts of dimethylformamide, and 15 parts of piperidine were added with stirring. After stirring for seven hours at room temperature, the precipitated product was filtered off with suction, washed with cold ethanol and dried at 50° C. in vacuo. This produced 394 parts (85% of theory) of a yellow dyestuff powder of the formula

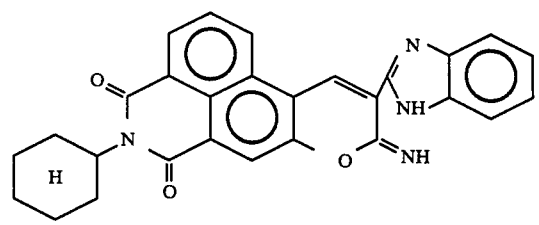

which gave brilliant yellow dyeings on polyester fiber materials.

EXAMPLE 4

313 parts of 3-hydroxy-4-formyl-N-(3-methoxy-n-propyl)-naphthalimide and 187 parts of 5-methoxy-2-cyanomethylbenzimidazole were suspended in 5000 parts of dimethylformamide, and 15 parts of pyrrolidine were added with stirring. After stirring for five hours at room temperature, the precipitated product was filtered off with suction, washed with cold ethanol and dried at 50° C. in vacuo. This produced 463 parts (96% of theory) of a red dyestuff powder of the formula

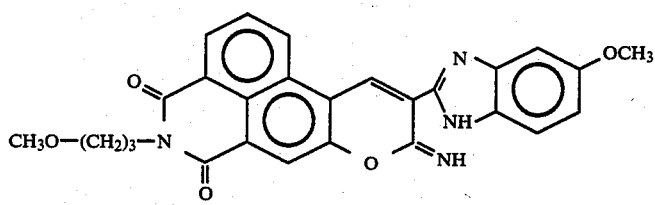

which gave brilliant orange dyeings on polyester fiber materials.

EXAMPLE 5

313 parts of 3-hydroxy-4-formyl-N-(3-methoxy-n-propyl)-naphthalimide and 217 parts of 5,6-dimethoxy-2-cyanomethylbenzimidazole were suspended in 2500 parts of dimethylformamide, and 10 parts of piperidine were added with stirring. After stirring for three hours at room temperature, the precipitated product was filtered off with suction, washed with cold ethanol and dried at 50° C. in vacuo. This produced 460 parts (90% of theory) of a dark red dyestuff powder of the formula

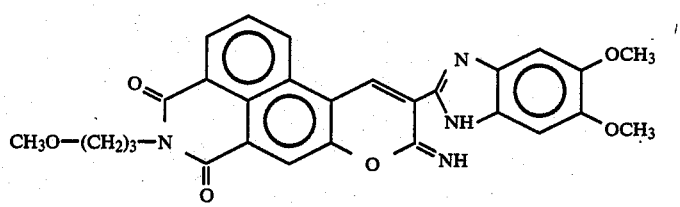

which gave red dyeings on polyester fiber materials.

When a procedure analogous to Examples 1-5 was followed, further dyestuffs according to the invention were obtained and they are listed in the table below:

General formula of the dyestuffs of Example 6-67 in the table below:

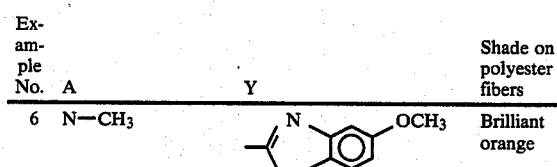

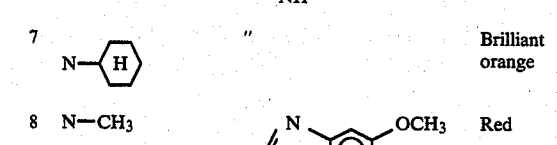

| Example No. | A | Y | Shade on polyester fibers |
|---|---|---|---|
| 6 | N—CH₃ | 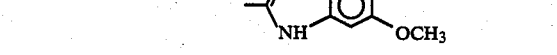 | Brilliant orange |
| 7 | N—⟨H⟩ | " | Brilliant orange |
| 8 | N—CH₃ |  | Red |
| 9 | " | " | Red |
| 10 | O | " | Red |
| 11 | N—CH₃ |  | Brilliant orange |
| 12 | N—(CH₂)₃—OCH₃ | " | Brilliant orange |
| 13 | O | " | Brilliant orange |
| 14 | N—⟨H⟩ | " | Brilliant orange |
| 15 | N—CH₃ |  | Red |
| 16 | N—(CH₂)₃—OCH₃ | " | Red |
| 17 | N—CH₃ |  | Red |
| 18 | N—(CH₂)₃—OCH₃ | " | Red |
| 19 | O |  | Brilliant yellow |
| 20 | N—⟨H⟩ | " | Brilliant yellow |

-continued

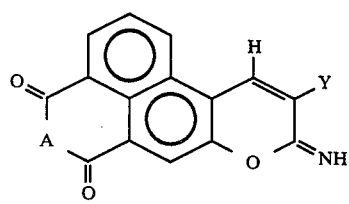

| Example No. | A | Y | Shade on polyester fibers |
|---|---|---|---|
| 21 | N—CH$_3$ | ![benzoxazole] | Brilliant greenish yellow |
| 22 | N—(CH$_2$)$_3$—OCH$_3$ | " | Brilliant greenish yellow |
| 23 | O | " | Brilliant greenish yellow |
| 24 | N—cyclohexyl(H) | " | Brilliant greenish yellow |
| 25 | N—CH$_3$ | 5-methylbenzoxazole | Brilliant greenish yellow |
| 26 | N—(CH$_2$)$_3$—OCH$_3$ | " | Brilliant greenish yellow |
| 27 | N—CH$_3$ | 6-methylbenzoxazole | Brilliant yellow |
| 28 | N—(CH$_2$)$_3$—OCH$_3$ | " | Brilliant yellow |
| 29 | N—CH$_3$ | " | Brilliant yellow |
| 30 | N—(CH$_2$)$_3$—OCH$_3$ | " | Brilliant yellow |
| 31 | N—CH$_3$ | 5,6-dimethylbenzoxazole | Brilliant yellow |
| 32 | N—(CH$_2$)$_3$—OCH$_3$ | " | Brilliant yellow |
| 33 | N—cyclohexyl(H) | " | Brilliant yellow |
| 34 | N—CH$_3$ | 5-methoxybenzoxazole | Brilliant yellow |
| 35 | N—(CH$_2$)$_3$—OCH$_3$ | 5-methoxybenzoxazole | Brilliant yellow |
| 36 | N—CH$_3$ | benzothiazole | Brilliant yellow |
| 37 | N—(CH$_2$)$_3$—OCH$_3$ | " | Brilliant yellow |

-continued

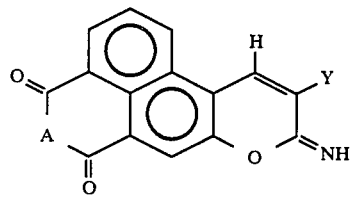

| Example No. | A | Y | Shade on polyester fibers |
|---|---|---|---|
| 38 | N—CH$_3$ | 6-methoxybenzothiazole | Brilliant yellow |
| 39 | N—(CH$_2$)$_3$—OCH$_3$ | " | Brilliant yellow |
| 40 | N—CH$_3$ | 6-methylbenzothiazole | Brilliant yellow |
| 41 | N—(CH$_2$)$_3$—OCH$_3$ | " | Brilliant yellow |
| 42 | N—CH$_3$ | 5-methylbenzimidazole | Brilliant yellow |
| 43 | N—(CH$_2$)$_3$—OCH$_3$ | " | Brilliant yellow |
| 44 | N—CH$_3$ | 5,6-dimethylbenzimidazole | Brilliant yellow |
| 45 | N—(CH$_2$)$_3$—OCH$_3$ | " | Brilliant yellow |
| 46 | N—CH$_3$ | 5-chlorobenzoxazole | Brilliant yellow |
| 47 | N—(CH$_2$)$_3$—OCH$_3$ | " | Brilliant yellow |
| 48 | N—CH$_3$ | 5,6-dichlorobenzoxazole | Brilliant yellow |
| 49 | N—(CH$_2$)$_3$—OCH$_3$ | " | Brilliant yellow |
| 50 | N—CH$_3$ | 5-chlorobenzimidazole | Brilliant yellow |
| 51 | N—(CH$_2$)$_3$—OCH$_3$ | " | Brilliant yellow |
| 52 | N—CH$_3$ | 5,6-dichlorobenzimidazole | Brilliant yellow |
| 53 | N—(CH$_2$)$_3$—OCH$_3$ | " | Brilliant yellow |

-continued

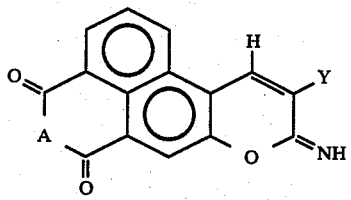

| Example No. | A | Y | Shade on polyester fibers |
|---|---|---|---|
| 54 | N—CH$_3$ | (benzothiazol-2-yl, 6-Cl) | Brilliant yellow |
| 55 | N—(CH$_2$)$_3$—OCH$_3$ | " | Brilliant yellow |
| 56 | N—CH$_3$ | (2-phenylbenzoxazol-yl) | Brilliant greenish yellow |
| 57 | N—(CH$_2$)$_3$—OCH$_3$ | " | Brilliant greenish yellow |
| 58 | N—CH$_3$ | (5-phenyl-1,3,4-thiadiazol-2-yl) | Brilliant greenish yellow |
| 59 | N—(CH$_2$)$_3$—OCH$_3$ | " | Brilliant greenish yellow |
| 60 | N—CH$_3$ | (5-(4-methoxyphenyl)-1,3,4-thiadiazol-2-yl) | Brilliant yellow |
| 61 | N—(CH$_2$)$_3$—OCH$_3$ | " | Brilliant yellow |
| 62 | N—CH$_3$ | (1-methylbenzimidazol-2-yl) | Brilliant yellow |
| 63 | N—(CH$_2$)$_3$—OCH$_3$ | " | Brilliant yellow |
| 64 | N—CH$_3$ | (1-ethylbenzimidazol-2-yl) | Brilliant yellow |
| 65 | N—(CH$_2$)$_3$—OCH$_3$ | | |
| 66 | N—CH$_3$ | 4-NO$_2$-C$_6$H$_4$ | Greenish yellow |
| 67 | N—(CH$_2$)$_3$—OCH$_3$ | 4-NO$_2$-C$_6$H$_4$ | Greenish yellow |
| 68 | N—Stearyl | (benzimidazol-2-yl) | Brilliant yellow |

EXAMPLE 69

255 parts of 3-hydroxy-4-formyl-N-methylnaphthalimide and 129 parts of benzyl cyanide were suspended in 3000 parts of methanol. 370 parts of a 30% strength methanolic sodium methanolate solution were added with stirring, and the resulting mixture was heated for 24 hours under reflux. The reaction mixture was diluted at 0°–5° C. with 1000 parts of water and adjusted with concentrated hydrochloric acid to pH 8. The precipitated product was filtered off with suction, washed with water until chloride-free and dried at 50° C. in vacuo. This produced 259 parts (73% of theory) of a yellow dyestuff powder of the formula

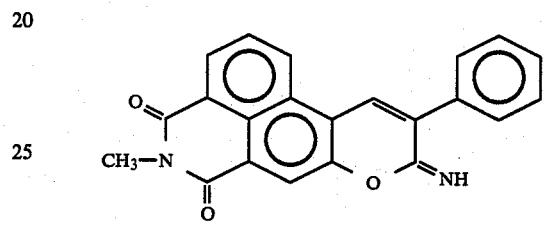

which gave greenish yellow dyeings on polyester fiber materials.

EXAMPLE 70

255 parts of 3-hydroxy-4-formyl-N-methylnaphthalimide and 130 parts of 2-pyridylacetonitrile were suspended in 2000 parts of methanol, 80 parts of potassium hydroxide were added with stirring, and the resulting mixture was heated for 90 hours under reflux. The reaction mixture was diluted at 0°–5° C. with 1000 parts of water and adjusted with concentrated hydrochloric acid to pH 8. The precipitated product was filtered off with suction, washed with water until chloride-free and dried at 50° C. in vacuo. This produced 290 parts (82% of theory) of a yellow dyestuff powder of the formula

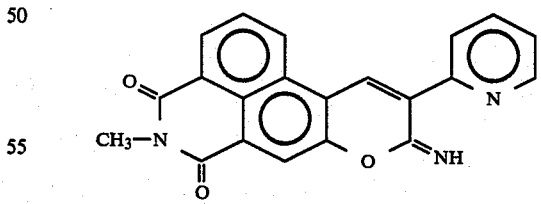

which gave greenish yellow dyeings on polyester fiber materials.

When a procedure analogous to Examples 69 and 70 was followed, further dyestuffs according to the invention were obtained and they are listed in the table below:

General formula of the dyestuffs of Examples 70–89 in the table below:

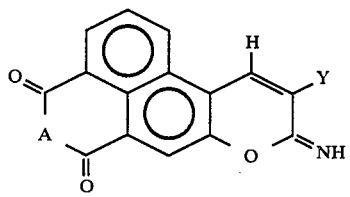

| Example No. | A | Y | Shade on polyester fibers |
|---|---|---|---|
| 71 | N—(CH₂)₃—OCH₃ | (phenyl) | Greenish yellow |
| 72 | N—(CH₂)₃—OCH₃ | (2-pyridyl) | " |
| 73 | N—CH₃ | (2-thienyl) | Brilliant yellow |
| 74 | N—(CH₂)₃—OCH₃ | " | " |
| 75 | N—(cyclohexyl)H | " | " |
| 76 | O | " | " |
| 77 | N—CH₃ | (4-methoxyphenyl) | Brilliant greenish yellow |
| 78 | N—(CH₂)₃—OCH₃ | " | " |
| 79 | N—CH₃ | (2-methoxyphenyl) | " |
| 80 | N—(CH₂)₃—OCH₃ | " | " |
| 81 | N—CH₃ | (4-methylphenyl) | " |
| 82 | N—(CH₂)₃—OCH₃ | " | " |
| 83 | N—CH₃ | (3,4-dimethoxyphenyl) | Brilliant yellow |
| 84 | N—(CH₂)₃—OCH₃ | " | " |
| 85 | N—CH₃ | (3,4-methylenedioxyphenyl) | " |

-continued

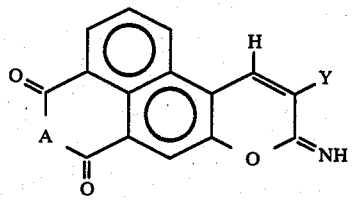

| Example No. | A | Y | Shade on polyester fibers |
|---|---|---|---|
| 86 | N—(CH₂)₃—OCH₃ | " | " |
| 87 | N—CH₃ | ![trimethoxyphenyl with OCH₃, OCH₃, OCH₃] | Brilliant golden yellow |
| 88 | N—(CH₂)₃—OCH₃ | " | " |
| 89 | N—cyclohexyl-H | " | " |

EXAMPLE 90

39.4 parts of the compound obtained according to Example 1 were suspended in 250 parts of pyridine, and 33.3 parts of stearyl chloride were added dropwise at 20° C. The mixture was stirred for 1 hour at room temperature and for 2 hours at 50° C. The precipitated product, after the reaction mixture had cooled down, was filtered off with suction, washed with hot water and ethanol and dried. This produced 42.9 parts (62% of theory) of a yellow dyestuff of the formula

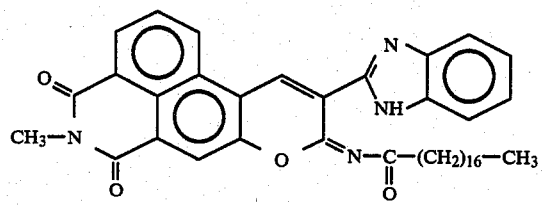

which gave brilliant yellow dyeings on polyester fiber materials.

EXAMPLE 91

42.3 parts of the dyestuff obtained according to Example 44 were suspended in 250 parts of pyridine. 20.9 parts of 4-toluenesulfonyl chloride were added to the suspension at room temperature, and the resulting mixture was stirred for 5 hours at room temperature. The precipitated reaction product was filtered off with suction, washed with ethanol and dried. This produced 50.7 parts (88% of theory) of a yellow dyestuff of the formula

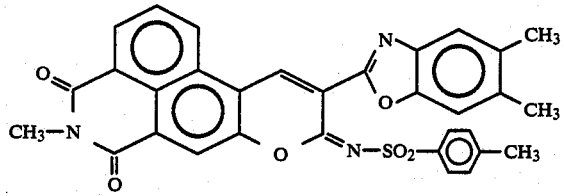

which gave brilliant yellow dyeings on polyester fiber materials.

EXAMPLE 92

42.3 parts of the dyestuff obtained according to Example 44 were suspended in 400 parts of dimethylformamide at 20° C., and 11.1 parts of triethylamine and 15 parts of n-butyl chloroformate were then successively added. The mixture was stirred for 3 hours at 40° C., and, after the reaction material had cooled down, the precipitated product was filtered off with suction, washed with ethanol and thereafter dried. This produced 35.6 parts (68% of theory) of a yellow dyestuff of the formula

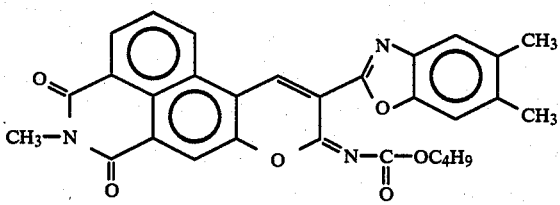

which gave brilliant yellow dyeings on polyester fiber materials.

EXAMPLE 93

44.4 parts of the dyestuff prepared according to Example 87 were heated for 3 hours at 135° C. together with 250 parts of acetic anhydride and 10.9 parts of sodium acetate. After cooling down to room temperature, the precipitated dyestuff was filtered off with suction, washed with water until neutral and thereafter dried. This produced 41.8 parts (86% of theory) of an orange-colored dyestuff of the formula

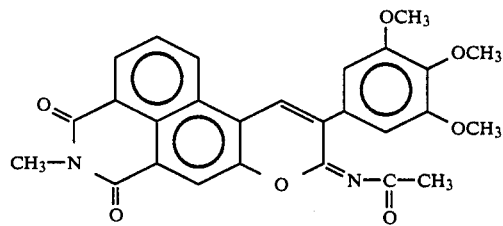

which gave brilliant, golden yellow dyeings on polyester fiber materials.

When a procedure analogous to Examples 90–93 was followed, further dyestuffs according to the invention were obtained and they are listed in the table below:

General formula of the dyestuffs of Examples 94–140 in the table below

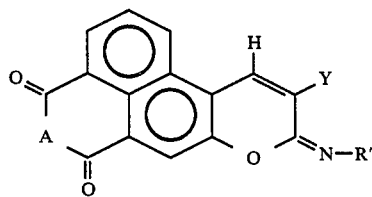

| Example No. | A | Y | R' | Shade on polyester fibers |
|---|---|---|---|---|
| 94 | N—(CH$_2$)$_3$—OCH$_3$ | (benzimidazolyl) | —O—CH$_3$ (C=O) | Brilliant yellow |
| 95 | " | " | —C(=O)—O—C$_2$H$_5$ | " |
| 96 | " | " | —SO$_2$CH$_3$ | " |
| 97 | " | " | —SO$_2$—C$_6$H$_4$—CH$_3$ | " |
| 98 | " | " | —C(=O)—(CH$_2$)$_{16}$—CH$_3$ | " |
| 99 | " | " | —C(=O)—C$_6$H$_5$ | " |
| 100 | " | " | —SO$_2$—C$_6$H$_5$ | " |
| 101 | N—CH$_3$ | " | —C(=O)—CH$_3$ | " |

-continued
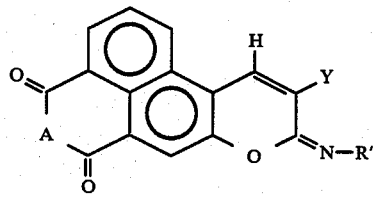
| Example No. | A | Y | R' | Shade on polyester fibers |
|---|---|---|---|---|
| 102 | N—(CH₂)₃—OCH₃ | ![benzimidazole-OCH₃] | —O—C(=O)—CH₃ | Brilliant orange |
| 103 | N—CH₃ | " | " | " |
| 104 | N—(CH₂)₃—OCH₃ | ![benzimidazole-di-OCH₃] | " | Red |
| 105 | N—CH₃ | " | " | " |
| 106 | N—(CH₂)₃—OCH₃ | ![dimethyl-benzoxazole] | " | Brilliant yellow |
| 107 | " | " | —C(=O)—OC₂H₅ | " |
| 108 | " | " | —C(=O)—(CH₂)₁₆CH₃ | " |
| 109 | " | " | —SO₂CH₃ | " |
| 110 | " | " | —SO₂—C₆H₅ | " |
| 111 | " | " | —C(=O)—OC₄H₉ | " |
| 112 | " | " | —SO₂—C₆H₄—CH₃ | " |
| 113 | N—CH₃ | " | —C(=O)—CH₃ | " |
| 114 | " | " | —C(=O)—OC₂H₅ | " |
| 115 | " | " | —C(=O)—(CH₂)₁₆CH₃ | " |
| 116 | " | " | —SO₂CH₃ | " |

-continued
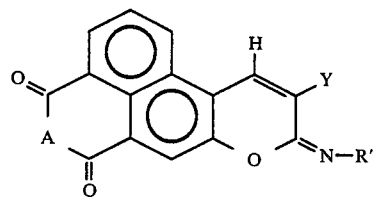
| Example No. | A | Y | R' | Shade on polyester fibers |
|---|---|---|---|---|
| 117 | " | " | −SO₂−C₆H₅ | " |
| 118 | " | " | −C(=O)−(CH₂)₂−CH₃ | " |
| 119 | O | 2-(5,6-dimethylbenzoxazolyl) | −O−C(=O)−CH₃ | " |
| 120 | N−(CH₂)₃−OCH₃ | 2,3,4-trimethoxyphenyl | " | Brilliant golden yellow |
| 121 | " | " | −C(=O)−CH₂−CH₃ | " |
| 122 | " | " | −C(=O)−CH(CH₃)₂ | " |
| 123 | " | " | −C(=O)−CH₂−CH₂−CH₃ | " |
| 124 | " | " | −C(=O)−(CH₂)₁₆CH₃ | " |
| 125 | " | " | −C(=O)−C₆H₅ | " |
| 126 | " | " | −C(=O)−C₆H₄−Cl | " |
| 127 | " | " | −SO₂−CH₃ | " |
| 128 | " | " | −SO₂−C₆H₅ | " |

-continued
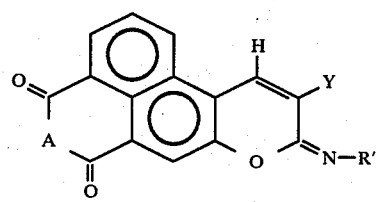
| Example No. | A | Y | R' | Shade on polyester fibers |
|---|---|---|---|---|
| 129 | " | " | —SO₂—C₆H₄—CH₃ | " |
| 130 | " | " | —C(O)—OCH₃ | " |
| 131 | " | " | —C(O)—OC₂H₅ | " |
| 132 | " | " | —C(O)—OC₄H₉ | " |
| 133 | N—CH₃ | " | —C(O)—CH₂—CH₃ | " |
| 134 | " | " | —C(O)—CH(CH₃)₂ | " |
| 135 | N—CH₃ | 2,3,4-(OCH₃)₃—C₆H₂— | —C(O)—CH₂—CH₂—CH₃ | " |
| 136 | " | " | —C(O)—(CH₂)₁₆—CH₃ | " |
| 137 | " | " | —C(O)—C₆H₅ | " |
| 138 | " | " | —SO₂—CH₃ | " |
| 139 | " | " | —SO₂—C₆H₅ | " |

-continued

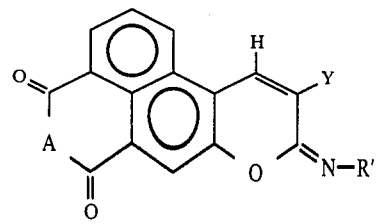

| Example No. | A | Y | R' | Shade on polyester fibers |
|---|---|---|---|---|
| 140 | " | " | −SO₂−⟨phenyl⟩−CH₃ | " |

EXAMPLE 141

39.4 parts of the dyestuff obtained according to Example 1 were stirred for 2 hours at 140° C. in 200 parts of aniline. At room temperature, the reaction product was precipitated by adding 200 parts of ethanol with stirring, filtered off with suction, washed with ethanol and dried. This produced 36.7 parts (78% of theory) of a red dyestuff powder of the formula

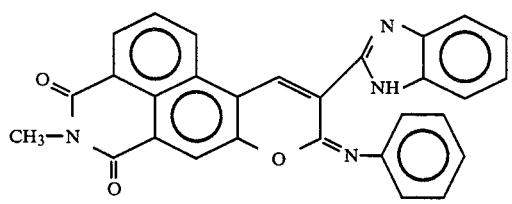

which gave bright orange dyeings on polyester fiber materials.

EXAMPLE 142

39.4 parts of the dyestuff obtained according to Example 1 and 12.2 parts of 4-methoxyaniline were stirred for 3 hours at 140° C. in 250 parts of dimethylformamide. At room temperature, the precipitated produce was filtered off with suction, washed with ethanol and dried. This produced 42.9 parts (86% of theory) of a red dyestuff powder of the formula

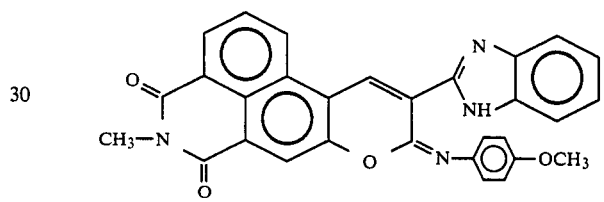

which gave orange dyeings on polyester fiber materials.

EXAMPLE 143

42.3 parts of the dyestuff obtained according to Example 31 were stirred for 2½ hours at 140° C. in 300 parts of aniline. At room temperature, 300 parts of ethanol were added with stirring and the precipitated product was filtered off with suction, washed with ethanol and thereafter dried. This produced 43.9 parts (83% of theory) of a red dyestuff of the formula

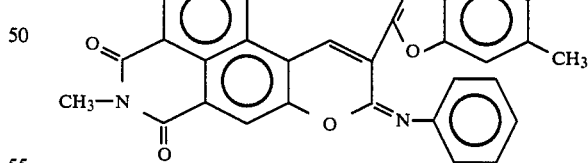

which gave orange dyeings on polyester fiber materials.

When a procedure analogous to Examples 141–143 was followed, further dyestuffs according to the invention were obtained and they are listed in the table below:

General formula of the dyestuffs of Examples 144–156 in the table below

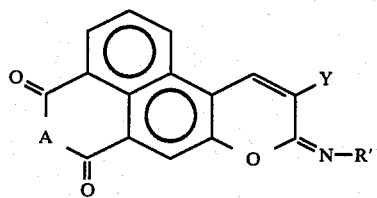
| Example No. | A | Y | R' | Shade on polyester fibers |
|---|---|---|---|---|
| 144 | N—(CH$_2$)$_3$—OCH$_3$ | 2-benzimidazolyl (NH) | phenyl | Orange |
| 145 | " | " | 4-methoxyphenyl | " |
| 146 | " | " | 4-cyanophenyl | " |
| 147 | N—CH$_3$ | " | 4-cyanophenyl | " |
| 148 | " | 5,6-dimethyl-2-benzoxazolyl | 4-methoxyphenyl | Red |
| 149 | " | " | 4-cyanophenyl | Orange |
| 150 | N—(CH$_2$)$_3$—OCH$_3$ | " | phenyl | " |
| 151 | " | " | 4-cyanophenyl | " |
| 152 | " | " | 4-methoxyphenyl | Red |
| 153 | " | 2-benzothiazolyl | phenyl | Orange |
| 154 | " | 2-benzoxazolyl | phenyl | Reddish yellow |

-continued

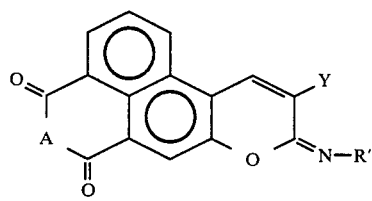

| Example No. | A | Y | R' | Shade on polyester fibers |
|---|---|---|---|---|
| 155 | " | ![OCH3 trimethoxyphenyl] with -OCH3, -OCH3, OCH3 | phenyl | " |
| 156 | CH$_3$ | " | -C$_6$H$_4$-OCH$_3$ | " |

EXAMPLE 157

39.5 parts of the dyestuff obtained according to Example 21 were suspended in 250 parts of chlorobenzene, 13.1 parts of phenyl isocyanate were added, and the resulting mixture was stirred for 18 hours at 80° C. After cooling down, the reaction product was filtered off with suction, washed with ethanol and dried. This produced 47.3 parts (92% of theory) of a yellow dyestuff of the formula

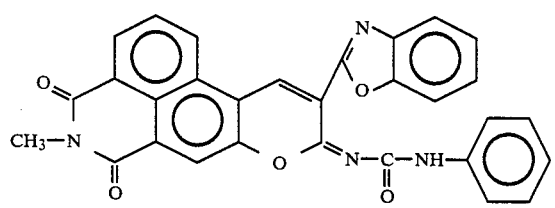

which gave greenish yellow dyeings on polyester fiber materials.

EXAMPLE 158

48.1 parts of the dyestuff obtained according to Example 32 were suspended in 400 parts of dioxan, 13.1 parts of phenyl isocyanate were added, and the resulting mixture was heated for 20 hours under reflux. After cooling down, the reaction product was filtered off with suction, washed with ethanol and dried. This produced 53.4 parts (89% of theory) of a yellow dyestuff of the formula

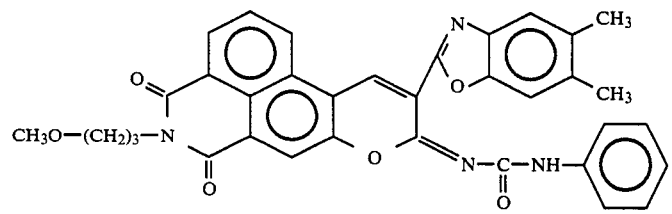

which gave brilliant, yellow dyeings on polyester fiber materials.

When a procedure analogous to Examples 157 and 158 was followed, further dyestuffs according to the invention were obtained and they are listed in the table below:

General formula of the dyestuffs of Examples 159–167 in the table below:

| Example No. | A | Y | Shade on polyester fibers |
|---|---|---|---|
| 159 | N—(CH$_2$)$_3$—OCH$_3$ | benzoxazol-2-yl | Brilliant yellowish green |

-continued

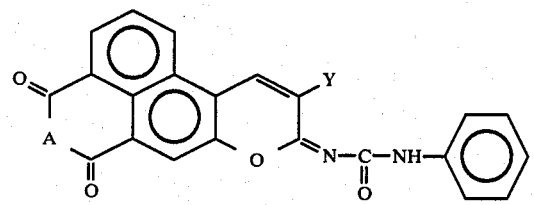

| Example No. | A | Y | Shade on polyester fibers |
|---|---|---|---|
| 160 | 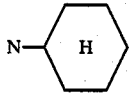 | " | Brilliant yellowish green |
| 161 | N—CH₃ | 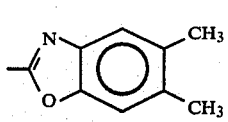 | Brilliant yellow |
| 162 | 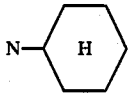 | " | Brilliant yellow |
| 163 | N—CH₃ | 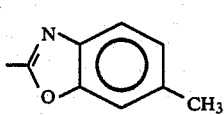 | Brilliant yellow |
| 164 | N—(CH₂)₃—OCH₃ | " | Brilliant yellow |
| 165 | N—CH₃ | 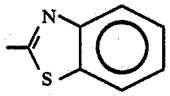 | Brilliant yellow |
| 166 | N—(CH₂)₃—OCH₃ | " | Brilliant yellow |
| 167 | N—CH₃ | 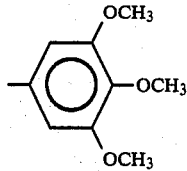 | Brilliant golden yellow |

EXAMPLE 168

255 parts of 3-hydroxy-4-formyl-N-methylnaphthalimide and 207 parts of methyl benzothiazole-2-acetate were refluxed for 4 hours under a water separator together with 10 parts of piperidine acetate in 6000 parts of toluene and 1000 parts of dimethylformamide. The reaction product was filtered off with suction at 0° C., washed with ethanol and dried. This produced 395.5 parts (96% of theory) of a yellow dyestuff of the formula

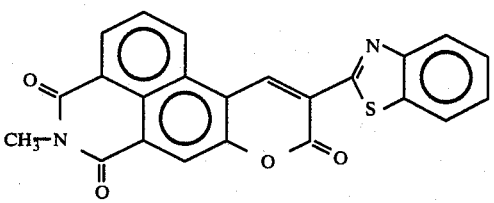

which gave brilliant yellow dyeings on polyester fiber materials.

EXAMPLE 169

255 parts of 3-hydroxy-4-formyl-N-methylnaphthalimide were stirred for 4 hours at 130° C. together with 5 parts of piperidine acetate in 3000 parts of diethyl malonate while volatile reaction products were removed by distillation. After cooling down to room temperature, the reaction product was filtered off with suction, washed with ethanol and dried. This produced 301.9 parts (86% of theory) of a yellow dyestuff of the formula

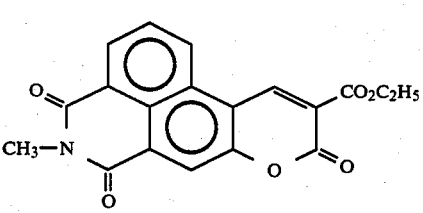

which gave greenish yellow dyeings on polyester fiber materials.

EXAMPLE 170

452 parts of the dyestuff prepared according to Example 2 were heated for 3 hours under reflux together with 6000 parts of 5% strength hydrochloric acid. After cooling down to room temperature, the reaction product was filtered off with suction, washed with water until chloride-free and dried. This produced 448.5 parts (99% of theory) of an orange-colored dyestuff powder of the formula

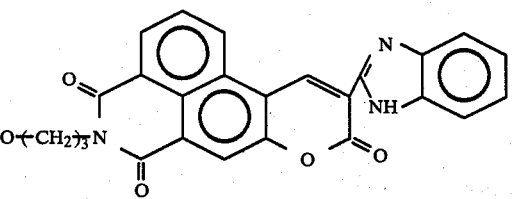

which gave brilliant yellow dyeings on polyester fiber materials.

EXAMPLE 171

255 parts of 3-hydroxy-4-formyl-N-methylnaphthalimide and 66 parts of malonic dinitrile were stirred at room temperature together with 10 parts of piperidine in 2500 parts of ethanol. After 4 hours, 1000 parts of water and 250 parts of concentrated hydrochloric acid were added, and the resulting mixture was boiled for 2 hours under reflux. The reaction product was filtered off with suction at room temperature, washed with water until chloride-free and dried. This produced 237 parts (78% of theory) of a yellow dyestuff powder of the formula

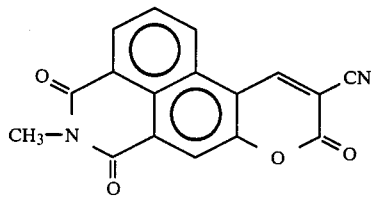

which gave greenish yellow dyeings on polyester fiber materials.

When a procedure analogous to Examples 168–171 was followed, further dyestuffs according to the invention were obtained and they are listed in the table below:

General formula of the dyestuffs of Examples 172–256 in the table below

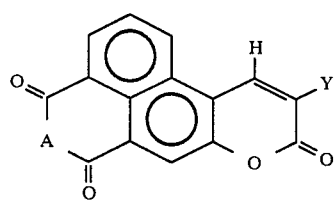

| Example No. | A | Y | Shade on polyester fibers |
|---|---|---|---|
| 172 | N—CH$_3$ | ⟨N,NH⟩-benzimidazolyl-OCH$_3$ | Brilliant orange |
| 173 | N—cyclohexyl-H | " | " |
| 174 | N—CH$_3$ | ⟨N,NH⟩-benzimidazolyl-(OCH$_3$)$_2$ | Red |
| 175 | N—cyclohexyl-H | " | " |
| 176 | O | " | " |
| 177 | N—CH$_3$ | ⟨N,NH⟩-benzimidazolyl-OC$_2$H$_5$ | Brilliant orange |
| 178 | N—(CH$_2$)$_3$—OCH$_3$ | " | " |
| 179 | O | " | " |
| 180 | N—cyclohexyl-H | " | " |
| 181 | N—CH$_3$ | ⟨N,NH⟩-benzimidazolyl-(OC$_2$H$_5$)$_2$ | Red |
| 182 | N—(CH$_2$)$_3$—OCH$_3$ | " | " |

-continued
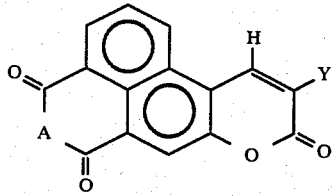
| Example No. | A | Y | Shade on polyester fibers |
|---|---|---|---|
| 183 | N—CH$_3$ | 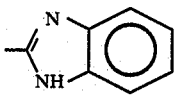 | " |
| 184 | N—(CH$_2$)$_3$—OCH$_3$ | " | " |
| 185 | N—CH$_3$ | 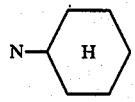 | Brilliant yellow |
| 186 | 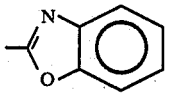 | " | " |
| 187 | N—CH$_3$ | 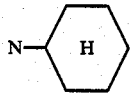 | Brilliant greenish yellow |
| 188 | N—(CH$_2$)$_3$—OCH$_3$ | " | " |
| 189 | O | " | " |
| 190 | 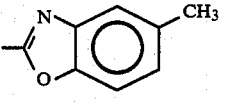 | " | " |
| 191 | N—CH$_3$ | 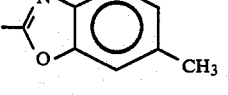 | " |
| 192 | N—(CH$_2$)$_3$—OCH$_3$ | " | " |
| 193 | N—CH$_3$ | 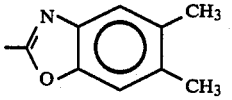 | Brilliant yellow |
| 194 | N—(CH$_2$)$_3$—OCH$_3$ | " | " |
| 195 | N—CH$_3$ | " | " |
| 196 | N—(CH$_2$)$_3$—OCH$_3$ | " | " |
| 197 | N—CH$_3$ | 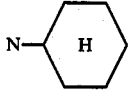 | " |
| 198 | N—(CH$_2$)$_3$—OCH$_3$ | " | " |
| 199 |  | " | " |

-continued

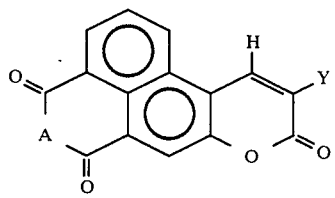

| Example No. | A | Y | Shade on polyester fibers |
|---|---|---|---|
| 200 | N—CH₃ | ![benzoxazole-OCH₃] | " |
| 201 | N—(CH₂)₃—OCH₃ | " | " |
| 202 | N—(CH₂)₃—OCH₃ | —CO₂C₂H₅ | Greenish yellow |
| 203 | N—(CH₂)₃—OCH₃ | ![benzothiazole] | Brilliant yellow |
| 204 | N—CH₃ | ![benzothiazole-OCH₃] | " |
| 205 | N—(CH₂)₃—OCH₃ | " | " |
| 206 | N—CH₃ | ![benzothiazole-CH₃] | " |
| 207 | N—(CH₂)₃—OCH₃ | " | " |
| 208 | N—CH₃ | ![benzimidazole-CH₃] | " |
| 209 | N—(CH₂)₃—OCH₃ | " | " |
| 210 | N—CH₃ | ![benzimidazole-diCH₃] | " |
| 211 | N—(CH₂)₃—OCH₃ | " | " |
| 212 | N—CH₃ | ![benzoxazole-Cl] | " |
| 213 | N—(CH₂)₃—OCH₃ | " | " |
| 214 | N—CH₃ | ![benzoxazole-diCl] | " |
| 215 | N—(CH₂)₃—OCH₃ | " | " |
| 216 | N—CH₃ | ![benzimidazole-Cl] | " |

-continued
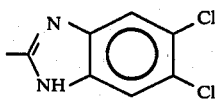
| Example No. | A | Y | Shade on polyester fibers |
|---|---|---|---|
| 217 | N—(CH$_2$)$_3$—OCH$_3$ | " | " |
| 218 | N—CH$_3$ | 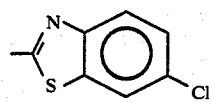 | " |
| 219 | N—(CH$_2$)$_3$—OCH$_3$ | " | " |
| 220 | N—CH$_3$ | 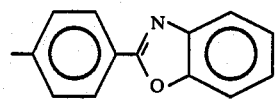 | " |
| 221 | N—(CH$_2$)$_3$—OCH$_3$ | " | " |
| 222 | N—CH$_3$ | 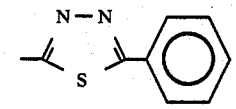 | Brilliant greenish yellow |
| 223 | N—(CH$_2$)$_3$—OCH$_3$ | " | " |
| 224 | N—CH$_3$ | 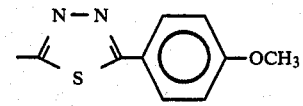 | " |
| 225 | N—(CH$_2$)$_3$—OCH$_3$ | " | " |
| 226 | N—CH$_3$ | 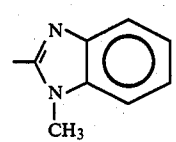 | Brilliant yellow |
| 227 | N—(CH$_2$)$_3$—OCH$_3$ | " | " |
| 228 | N—CH$_3$ | 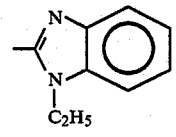 | " |
| 229 | N—(CH$_2$)$_3$—OCH$_3$ | " | " |
| 230 | N—CH$_3$ | 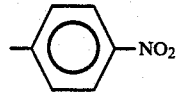 | " |
| 231 | N—(CH$_2$)$_3$—OCH$_3$ | " | " |
| 232 | N—CH$_3$ | —⟨phenyl⟩—NO$_2$ | Greenish yellow |
| 233 | N—(CH$_2$)$_3$—OCH$_3$ | " | " |

-continued
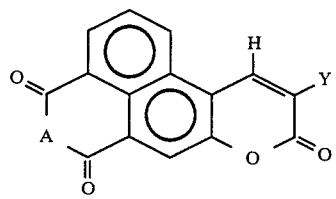
| Example No. | A | Y | Shade on polyester fibers |
|---|---|---|---|
| 234 | N—(CH₂)₃—OCH₃ | phenyl | " |
| 235 | N—(CH₂)₃—OCH₃ | 2-pyridyl | " |
| 236 | N—CH₃ | 2-thienyl | Brilliant yellow |
| 237 | N—(CH₂)₃—OCH₃ | " | " |
| 238 | N—cyclohexyl | " | " |
| 239 | O | " | " |
| 240 | N—CH₃ | 4-methoxyphenyl | Brilliant greenish yellow |
| 241 | N—(CH₂)₃—OCH₃ | " | " |
| 242 | N—CH₃ | 3,4-dimethoxyphenyl (with OCH₃) | " |
| 243 | N—(CH₂)₃—OCH₃ | " | " |
| 244 | N—CH₃ | 4-methylphenyl | " |
| 245 | N—(CH₂)₃—OCH₃ | " | " |
| 246 | N—CH₃ | 2,3-dimethoxyphenyl | Brilliant yellow |
| 247 | N—(CH₂)₃—OCH₃ | " | " |

-continued

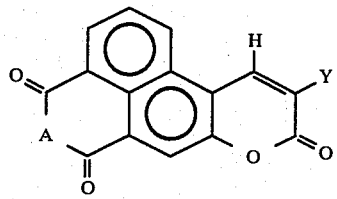

| Example No. | A | Y | Shade on polyester fibers |
|---|---|---|---|
| 248 | N—CH₃ | ![dioxole-CH3 group] | " |
| 249 | N—(CH₂)₃—OCH₃ | " | " |
| 250 | N—CH₃ | ![trimethoxyphenyl] | Brilliant golden yellow |
| 251 | N—(CH₂)₃—OCH₃ | " | " |
| 252 | N—cyclohexyl-H | " | " |
| 253 | N—(CH₂)₃—OCH₃ | —CN | Greenish yellow |
| 254 | N—(CH₂)₃—OCH₃ | —CO₂C₂H₅ | " |
| 255 | N—(CH₂)₃—OCH₃ | —SO₂—phenyl | Brilliant greenish yellow |
| 256 | N—CH₃ | " | " |

EXAMPLE 257

77 parts of the dyestuff prepared according to Example 240 were suspended in 500 parts of dimethylformamide, and 60 parts of a 30% strength potassium cyanide solution were added dropwise at room temperature. The mixture was heated for 4 hours at 60° C. and cooled down to −5° C., 11.2 parts of bromine were added dropwise, and the resulting mixture was stirred for 5 hours at room temperature. The resulting product of the formula

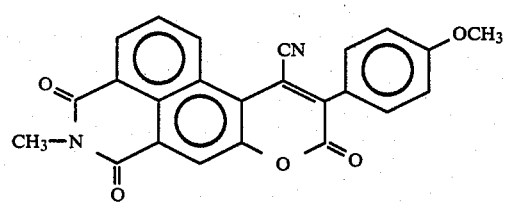

was filtered off with suction, washed with water until bromide-free and dried. This produced 56.6 parts (69% of theory) of a red dyestuff which gave brilliant yellow dyeings on polyester fiber materials.

EXAMPLE 258

84.8 parts of the dyestuff prepared according to Example 197 were suspended in 1000 parts of dimethylformamide, and 60 parts of a 30% strength potassium cyanide solution were added dropwise at room temperature. The mixture was stirred for two hours at room temperature and cooled down to −5° C., 11.2 parts of bromine were added dropwise, and the resulting mixture was stirred for 4 hours at room temperature. The precipitated product of the formula

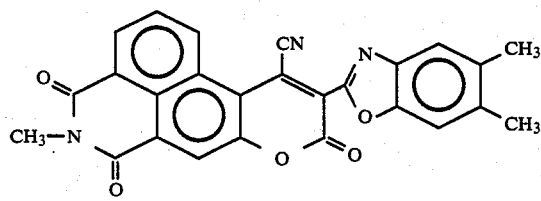

was filtered off with suction, washed with water until bromide-free and dried. This produced 68.2 parts (76% of theory) of a red dyestuff which gave brilliant orange dyeings on polyester fiber materials.

When a procedure analogous to Examples 257 and 258 was followed, further dyestuffs according to the invention were obtained and they are listed in the table below:

General formula of the dyestuffs of Examples 259–277 in the table below

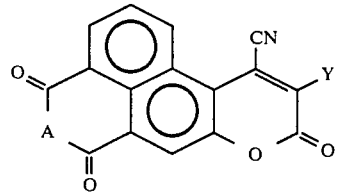

| Example No. | A | Y | Shade on polyester fibers |
|---|---|---|---|
| 259 | N—(CH$_2$)$_3$—OCH$_3$ | ―⟨⟩—OCH$_3$ | Brilliant yellow |
| 260 | N—(CH$_2$)$_3$—OCH$_3$ | benzoxazole with 2 CH$_3$ | Brilliant orange |
| 261 | N—CH$_3$ | benzimidazole (NH) | Brilliant orange |
| 262 | N—(CH$_2$)$_3$—OCH$_3$ | " | Brilliant orange |
| 263 | cyclohexyl-H | " | Brilliant orange |
| 264 | N—CH$_3$ | benzothiazole | Brilliant orange |
| 265 | N—(CH$_2$)$_3$—OCH$_3$ | " | Brilliant orange |
| 266 | N—CH$_3$ | benzoxazole | Brilliant yellow |
| 267 | N—(CH$_2$)$_3$—OCH$_3$ | " | Brilliant yellow |
| 268 | N—CH$_3$ | benzoxazole-CH$_3$ | Brilliant orange |

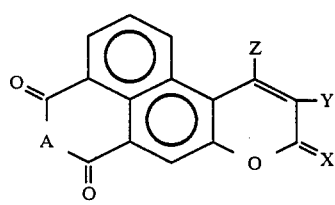

| Example No. | A | Y | Shade on polyester fibers |
|---|---|---|---|
| 269 | N—(CH$_2$)$_3$—OCH$_3$ | " | Brilliant orange |
| 270 | N—CH$_3$ | thiophene | Brilliant orange |
| 271 | N—(CH$_2$)$_3$—OCH$_3$ | " | Brilliant orange |
| 272 | N—CH$_3$ | methylenedioxyphenyl | Brilliant orange |
| 273 | N—(CH$_2$)$_3$—OCH$_3$ | " | Brilliant orange |
| 274 | N—CH$_3$ | ―⟨⟩ with OCH$_3$, OCH$_3$ | Brilliant orange |
| 275 | N—(CH$_2$)$_3$—OCH$_3$ | " | Brilliant orange |
| 276 | N—CH$_3$ | ―⟨⟩ with OCH$_3$, OCH$_3$, OCH$_3$ | Red |
| 277 | N—(CH$_2$)$_3$—OCH$_3$ | " | Red |

We claim:
1. A coumarin of the formula in which
A is >N—R wherein R is hydrogen, alkyl of from 1 to 18 carbon atoms, or alkyl of from 1 to 18 carbon atoms mono-, di- or trisubstituted by fluorine, chlorine or bromine, or mono- or disubstituted by alkoxy of from 1 to 4 carbon atoms, dialkylamino of from 2 to 8 carbon atoms, sulfodialkylamide of from 2 to 8 carbon atoms or cyano, the di- or tri-substituents being the same or not all the same; or is a moiety selected from the group consisting of cyclopentyl, cyclohexyl, cycloheptyl, phenyl, naphthyl, pyridyl, pyrimidyl, benzoxazolyl, benzothiozolyl and benzimidazolyl, or said moiety mono-, di- or trisubstituted at one or more nuclear carbon atoms by fluorine, chlorine or bromine, or mono- or disubstituted at one or more nuclear carbon atoms by alkyl of from 1 to 4 carbon atoms, alkoxy of from 1 to 4 carbon atoms, hydroxyl, cyano, sulfonamide or sulfodialkyl-amide of from 2 to 8 carbon atoms, the di- or tri-substituents being the same or not all the same;

X is oxygen or >N—R' wherein R' is
a moiety selected from the group consisting of hydrogen, alkylcarbonyl of from 2 to 19 carbon atoms, alkoxycarbonyl of from 2 to 5 carbon atoms, alkylcarbamoyl of from 2 to 5 carbon atoms and alkylsulfonyl of from 1 to 4 carbon atoms, or said moiety mono-, di- or trisubstituted in the alkyl or alkoxy group by fluorine, chlorine or bromine, or mono- or disubstituted in the alkyl or alkoxy group by alkoxy of from 1 to 4 carbon atoms or cyano, the di- or tri-substituents being the same or not at all the same; or is phenyl, phenylcarbonyl, phenycarbamoyl or phenysulfonyl, or phenyl, phenylcarbonyl, phenylcarbanoyl or phenylsulfonyl mono-, di- or trisubstituted in the phenyl moiety by fluorine, chlorine, bromine, alkyl of from 1 to 4 carbon atoms, alkoxy of from 1 to 4 carbon atoms, nitro, or cyano, the di- or tri-substituents being the same or not all the same;

Y is
hydrogen, cyano, or alkyl carboxylate of from 2 to 5 carbon atoms, phenyl, phenylsulfonyl or phenylcarboxylate, or phenyl, phenylsulfonyl or phenylcarboxylate mono-, di- or trisubstituted in the phenyl group by fluorine, chlorine or bromine, alkyl of from 1 to 4 carbon atoms or alkoxy of from 1 to 4 carbon atoms, or mono- or disubstituted in the phenyl group by nitro, amino, monoalkyl or dialkylamino wherein said alkyl is of from 1 to 4 carbon atoms, or monosubstituted in the phenyl group by methylenedioxy or benzoxazolyl, the di- or tri-substituents being the same or not at all the same, or is a moiety selected from the group consisting of thienyl, benzothienyl, furyl, benzofuryl, triazolyl, imidazolyl, benzimidazolyl, thiazolyl, benzothiazolyl, oxazolyl, benzoxazolyl, thiadiazolyl, oxadiazolyl or pyridyl, or said moiety mono-, di- or trisubstituted at one or more nuclear carbon atoms by fluorine, chlorine, bromine, alkyl of from 1 to 4 carbon atoms or alkoxy of from 1 to 4 carbon atoms, or mono- or disubstituted at one or more nuclear carbon atoms by nitro, phenyl, alkylphenyl wherein said alkyl is of from 1 to 4 carbon atoms, alkoxyphenyl wherein said alkoxy is of from 1 to 4 carbon atoms, or cyano, or monosubstituted at a nuclear carbon atom by methylenedioxy or alkylcarboxylate of from 2 to 5 carbon atoms, the di- or trisubstituents being the same or not all the same; and Z is hydrogen, cyano or alkylcarboxylate of from 2 to 5 carbon atoms.

2. A coumarin compound as claimed in claim 1, in which A is >N—R wherein R is methyl, methoxypropyl, stearyl or cyclohexyl; X is oxygen or >N—R' wherein R' is hydrogen, acetyl, chloroacetyl, propionyl, n-butyryl, isobutyryl, stearyl, methoxycarbonyl, ethoxycarbonyl, methoxyethoxycarbonyl, butoxycarbonyl, phenoxycarbonyl, diethylaminocarbonyl, methylsufonyl, cyanomethylsulfonyl, ethylsulfonyl, chloroethylsulfonyl, methoxypropylsulfonyl, phenyl, methoxyphenyl, cyanophenyl, benzoyl, chlorobenzoyl, nitrobenzoyl, dinitrobenzoyl, phenylacryloyl, phenylcarbamoyl, phenylsulfonyl or tolylsulfonyl; Y is cyano, ethoxycarbonyl, phenyl, nitrophenyl, methoxyphenyl, dimethoxyphenyl, trimethoxyphenyl, tolyl, methylenedioxyphenyl, benzoxazolylphenyl, phenylsulfonyl, phenoxycarbonyl, benzimidazolyl, chlorobenzimidazolyl, dichlorobenzimidazolyl, methylbenzimidazolyl, dimethylbenzimidazolyl, methoxybenzimidazolyl, dimethoxybenzimidazolyl, ethoxybenzimidazolyl, diethoxybenzimidazolyl, methylenedioxybenzimidazolyl, N-methylbenzimidazolyl, N-ethylbenzimidazolyl, benzoxazolyl, chlorobenzoxaxolyl, dichlorobenzoxazolyl, methylbenzoxazolyl, dimethylbenzoxazolyl, methoxybenzoxazolyl, benzthiazolyl, chlorobenzthiazolyl, methylbenzthiazolyl, methoxybenzthiazolyl, phenylthiadiazolyl, methoxyphenylthiadiazolyl, pyridyl or thienyl; and Z is hydrogen or cyano.

3. The coumarin compound of the formula

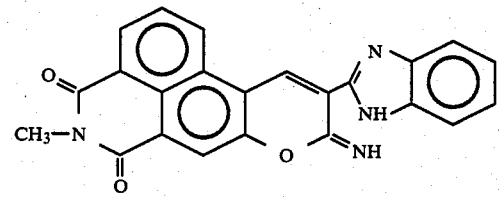

4. The coumarin compound of the formula

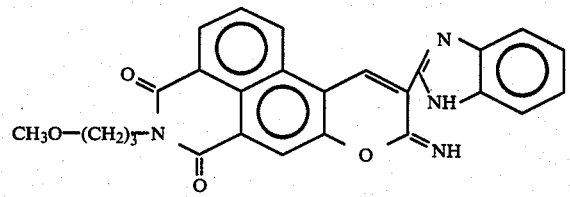

5. The coumarin compound of the formula

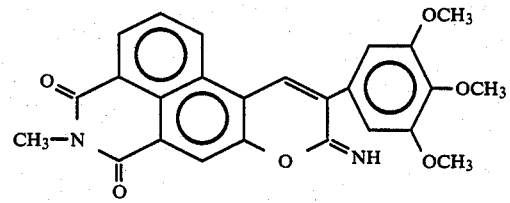

6. The coumarin compound of the formula

7. The coumarin compound of the formula
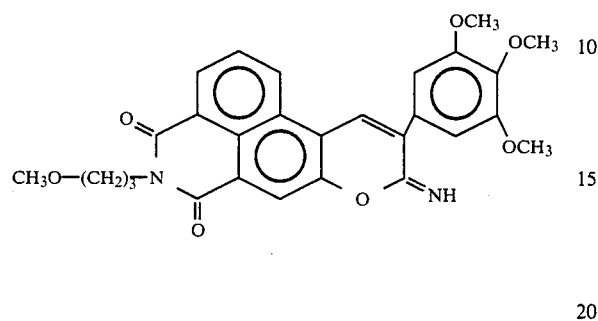
8. The coumarin compound of the formula
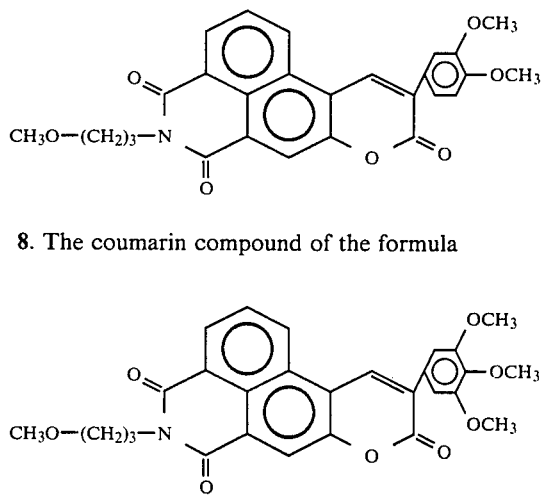
* * * * *